Figure 7:
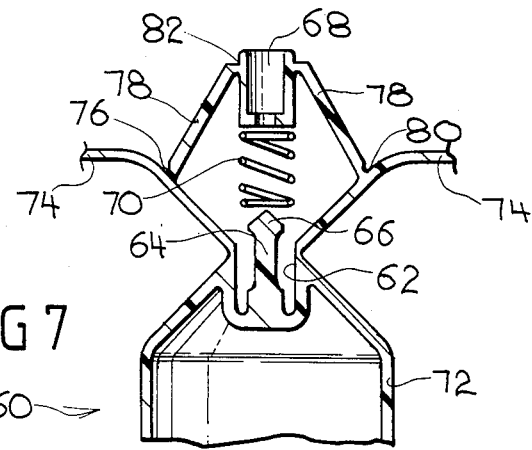

United States Patent [19]

Laby et al.

[11] Patent Number: 4,687,480
[45] Date of Patent: Aug. 18, 1987

[54] CONTROLLED RELEASE CAPSULE

[75] Inventors: Ralph H. Laby, Canterbury; Mark A. Lance, South Melbourne, both of Australia

[73] Assignee: Commonwealth Scientific and Industrial Research Organization, Campbell, Australia

[21] Appl. No.: 774,053

[22] Filed: Sep. 9, 1985

[30] Foreign Application Priority Data

Sep. 14, 1984 [AU] Australia ............... PG7116

[51] Int. Cl.$^4$ ............................................. A61K 9/22
[52] U.S. Cl. ..................................... 604/891; 604/105
[58] Field of Search ................ 604/890, 891, 892, 93, 604/105, 106

[56] References Cited

U.S. PATENT DOCUMENTS

| | | | |
|---|---|---|---|
| 3,656,483 | 4/1972 | Rudel | 604/892 |
| 3,765,414 | 10/1973 | Arlen | 604/891 |
| 3,797,492 | 3/1974 | Place | 604/890 |
| 4,410,328 | 10/1983 | Theeuwes | 604/890 |

FOREIGN PATENT DOCUMENTS

| | | |
|---|---|---|
| 449029 | 5/1972 | Australia . |
| 470538 | 11/1974 | Australia . |
| 6977974 | 11/1976 | Australia . |
| 7778281 | 7/1980 | Australia . |
| 9010882 | 11/1981 | Australia . |
| 520409 | 1/1982 | Australia . |
| 1163983 | 8/1983 | Australia . |
| 555998 | 10/1986 | Australia . |
| WO81/00082 | 7/1981 | PCT Int'l. Appl. . |

Primary Examiner—John D. Yasko
Attorney, Agent, or Firm—Merchant, Gould, Smith, Edell, Welter & Schmidt

[57] ABSTRACT

A device for the sustained release of into the rumen of a ruminant animal has an elongate, tubular body for housing a therapeutic or nutrient composition. Wings are pivotably attached to one end of the body member and are resumably biased away from a storage position, in which they extend along body member, an operative position. In the operative position, the wings are at a pre-determined angle to the longitudinal extent of the body member and are constrained from pivoting beyond this angle.

18 Claims, 10 Drawing Figures

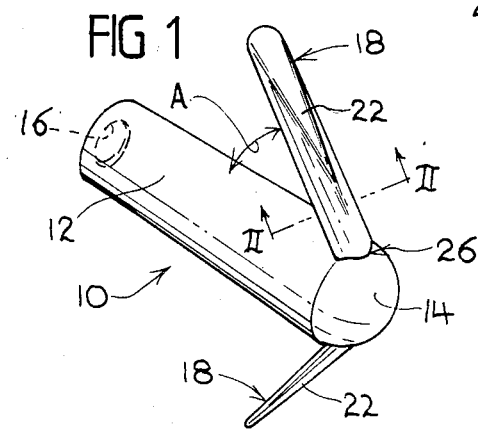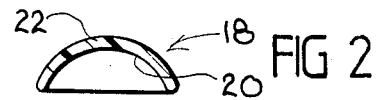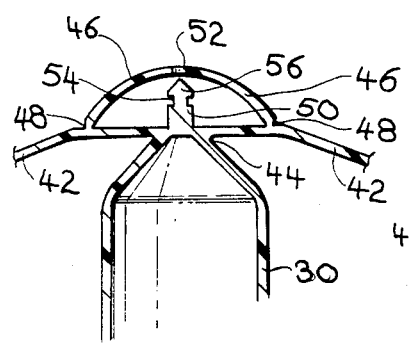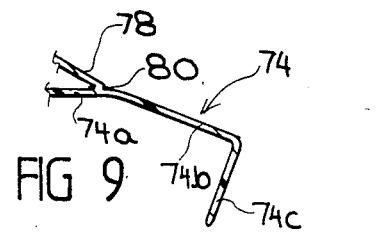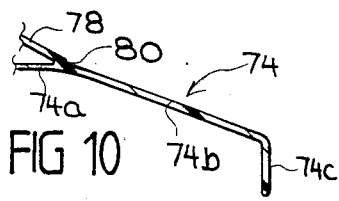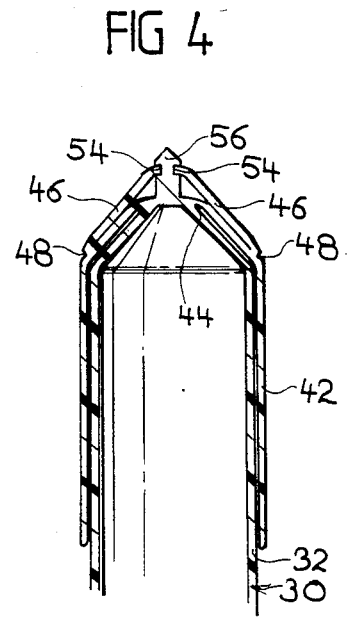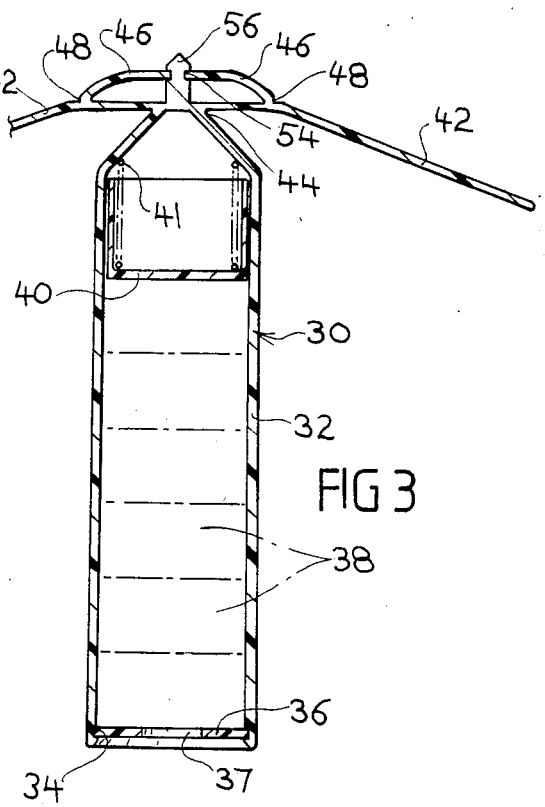

CONTROLLED RELEASE CAPSULE

This invention relates to devices for the sustained release of materials into the rumen of ruminant animals, and in particular it concerns means for ensuring the retention of such devices in the rumen.

For many years it has been recognized that there are circumstances when it is desirable to supply animals with medicaments, trace elements and the like, continuously and over an extended period. Our Australian Pat. No. 449029 introduced the general concept of meeting such requirements in the case of ruminant animals by a capsule which could be introduced into the rumen via the oesophagus, but which adopted a shape in the rumen that prevented it being regurgitated while a bioactive payload was slowly released. Our Australian Pat. No. 520409 disclosed a particular form of such a capsule comprising a substantially cylindrical plastic body having wings integrally molded therewith and in which elasticity of the plastic at the point of attachment to the body permits the wings to be folded along the body to facilitate the passage down the oesophagus and to cause the wings to extend away from the body when in the rumen.

While devices such as described in Australian Pat. No. 520409 are generally satisfactory, simple-one point attachment of wings to the capsule body can introduce functional problems in that, unless the wing/body hinge is of relatively massive proportions, the wings may assume the position of the arms of a Y so that there is an increased risk of the capsule being regurgitated. Also if, as generally is a practical necessity, such capsules are stored for prolonged periods with their wings in the folded position, the "creep" or loss of memory, inherent in plastic materials with passage of time, can lead to failure of the wings to assume a sufficiently extended position after insertion in the rumen.

In its general form, a capsule according to the present invention comprises an elongate, tubular body member for housing a quantity of a therapeutic or nutrient composition for sustained release in the rumen of an animal to which the capsule is administered; and a plurality of elongate wings, each pivotally attached at one end thereof to the body member in the vicinity of one end (hereinafter referred to as the "leading end") of the latter; each wing being resiliently biased away from a storage position, to which it is pivotable so as to extend along the body member, toward the other (trailing) end thereof, to a laterally extending operative position in which it is at a predetermined angle to the body member, and being constrained against pivoting beyond such angle.

In each form of the invention, the wings preferably are formed integrally with the body member, such as by injection moulding from a suitable plastics material. However, the wings may be similarly formed with a portion of the body member, such as an end cap thereof. In the latter case, the portion of the body member may be connected to the remaining portion of the member by snap-fit or screw-threaded engagement between those portions, or adhesively bonding the portions.

In a first embodiment of the invention, each wing is of arcuate form transversely of its longitudinal extent. Each wing thus defines a concave surface; such surface being that one which, with the wing in its storage position, contacts the body member; with the surface of the wing remote from that concave surface being convex. In such embodiment, each wing merges with the body member along a curved, integral hinge connection which is of a curvature corresponding to the curvature of the concave and convex surfaces. The transverse curvature of each wing and its junction with the body member enables pivoting of the wing, at its hinge connection, to a storage position in which it extends along the body member. Also, such transverse curvature and junction provides a constraint acting against pivoting of each wing away from its storage position substantially beyond its operative position. Preferably, a bead is provided along the hinge connection, at the junction of the convex surface and the body member, to further constrain the wing from moving beyond its operative position.

The predetermined angle is less than 90°, preferably less than 80°, such as about 70°-75°. Where, in that first embodiment of the invention, the wings are held in their storage position, and retained in that position by an encircling band for a substantial period, the wings will only partially return to their as-formed position due to resultant creep in the material from which it is formed. It therefore is preferred that the capsule, as-formed, has its wings extending at a greater angle than the predetermined angle such that, on release from their storage position, the wings attain substantially the required predetermined angle.

In a second embodiment, the capsule includes strut means which is pivotally connected to each wing and which extends across the leading end of the body member. Most conveniently, the strut means is connected to the body member, such as at a location further from the trailing end of the body member than the connection of each wing member. However, it is not essential that the strut means is connected to the body member.

In the second embodiment, the strut means may comprise a curved strut which, at each end thereof, is pivotally attached to a respective wing at a location spaced from the body member by a minor proportion of the length of each wing. The curved strut extends across the leading end of the body member, and preferably it is connected intermediate its ends to the body member. Connection between the strut and the body member may be by means of a screw passing through the strut member and axially into the body member. Alternatively, the connection may be by means of a snap-fit engagement between a projection on one of the strut and body member and an aperture defined on the other of the strut and body member. Most preferably, the body member has at its leading end an axially extending stud having an enlarged head, with the strut having an aperture which is received by a snap-fit onto the stud, so that the strut is retained on the stud by the enlarged head.

In such second embodiment, the curvature of the strut enables pivoting of each wing from its operative position so as to extend along, and against, the body member in a storage position. However, the "memory" of the strut acts to urge the wings to their operative position; while the compressive strength of the strut is such that the strut provides a constraint acting against pivoting of the wings away from their storage position substantially beyond their operative position.

In a third embodiment, the capsule has biasing means acting between the body member and the wings so as to normally urge the wings toward their operative position. Also, the capsule has stop means operative to prevent movement of the wings away from their storage position, beyond the operative position.

In the third embodiment, the capsule preferably has an abutment member located axially beyond the leading end of the body member. In such case, one of the abutment member and the body member may have an axial projection slidable in an aperture of the other of those members, such that the abutment member is movable axially, toward and away from, the leading end of the body member between inner and outer limiting positions. Biasing means, such as a helical spring surrounding the projection, preferably acts to urge the abutment member towards its outer position, while an enlargement on the axial projection preferably acts as a stop member which limits the axial distance between those limiting positions. A respective strut member preferably is pivotally connected at one end to each wing, with the other end of each strut member pivotally connected to the abutment member. In that arrangement, movement of the abutment member is transferred to the wing members such that, in urging the abutment member to its outer limiting position, the biasing means acts to bias the wings to their operative position. The stop members acts to limit movement of the wings beyond that position. However, the wings are able to be pivoted to their storage position, against the action of the biasing means.

With the wings of the capsule according to the invention in their operative position, an encircling band can be placed around the capsule to retain the wings in that position. The capsule preferably is administered to an animal with the wings so retained so that the capsule passes into the animal's rumen in that condition, via the animal's oesophagus. The band therefore preferably is of a material which will rapidly disintegrate in rumen fluid, to allow the wings to be moved to their operative position under the action of the biasing means.

Figure 8:
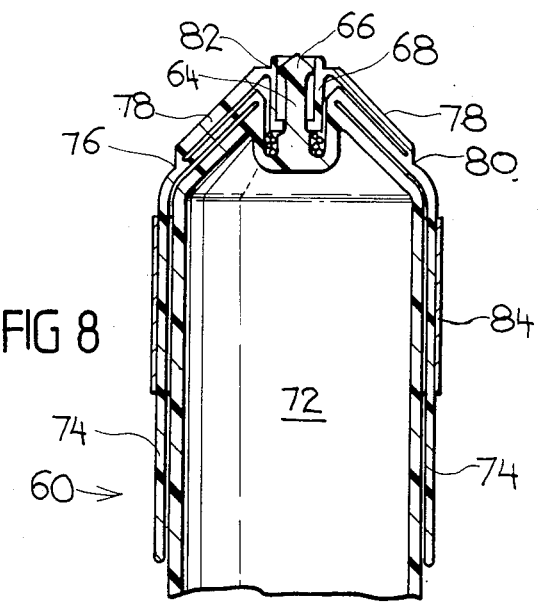
Figure 6:
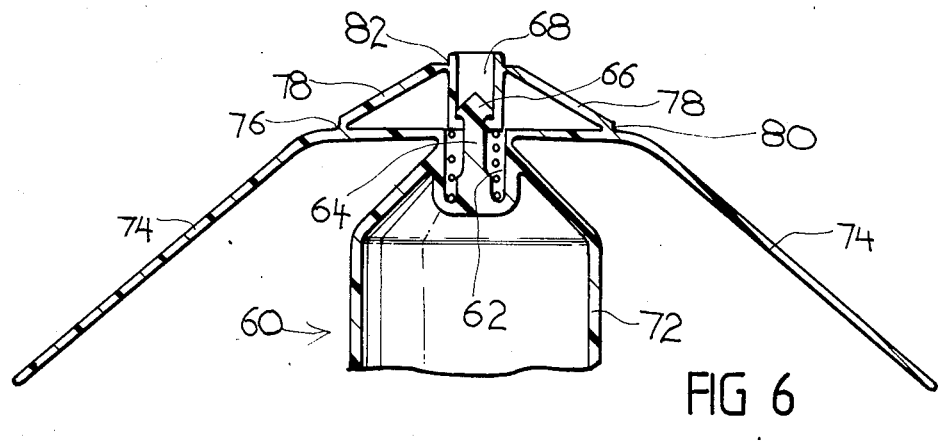

Description now is directed to the accompanying drawings, in which:

FIG. 1 is a perspective view of a first capsule;
FIG. 2 is a sectional view on line II—II of FIG. 1;
FIG. 3 is a longitudinal sectional view of a second capsule;
FIGS. 4 and 5 show partial views corresponding to FIG. 3, with the capsule in different respective conditions:
FIGS. 6, 7 and 8 correspond to FIG. 3, 4 and 5, but show a third capsule; and
FIGS. 9 and 10 show modifications possible in the capsules of FIGS. 1, 3 and 6.

With reference to FIGS. 1 and 2, the capsule 10 has a body 12 and, at the leading end of body 12, a cap 14. Body 10 is of hollow, cylindrical form and has an integral end wall at its trailing end which defines an access opening 16. Prior to fitting cap 14 onto body 12, a therapeutic or nutrient composition is inserted into body 10, after which plunger means such as shown in FIG. 3, is inserted into body 12.

Capsule 10 has an opposed pair of wings 18 which project outwardly from cap 14 at a predetermined angle A, such as of 75°. As shown in FIG. 1, wings 18 are in their operative position. Wings 18 are formed integrally with cap 14; capsule 10 preferably being injection moulded from polypropylene, polyethene or other suitable thermoplastic material. As shown in FIG. 2, each wing 18 is of arcuate transverse section, having a concave inner surface 20 and a corresponding convex outer surface 22. Each wing 18 is connected to cap 14 along a similarly arcuate hinge line 26; the arrangement being such that each wing can be pivoted on line 26 to a storage position in which its surface 20 is in contact with body 12. The arcuate form of wings 18 is such that they fit snugly against body 12, when in their storage position. However, on release from that position, wings 18 return to their operative position as shown due to the memory of the material forming hinge line 26 and the adjacent retions of wings 18 and cap 14. Also, wings 18 are constrained against movement beyond the operative position by their curvature and the curved hinge line 26, and resultant sharply increasing compressive forces generated in the material of hinge 26 adjacent wing surface 22.

Wings 18 may be of constant curvature along their length. However, the curvature preferably decreases away from cap 14, with the wings being substantially flatter or flat at their outer ends. Such decrease in curvature, optionally accompanied by correspondingly decreasing thickness of wings 18, is preferred since forces exerted on capsule 10 by rumen musculature largely are distributed over the entire length of the wing. Thus, the forces are dissipated in resilient flexing of wings 18, rather than applied to line 26, and so do not bend wings 18 beyond their operative position, such as to a Y configuration enabling regurgitation.

With reference to FIGS. 3 to 5, the capsule 30 shown therein has an elongate, hollow cylindrical body 32, which is closed at its leading end and open at its trailing end. Within groove 34 defined at the trailing end, an annular disc 36 is snap-fitted to retain tablets 38 of therapeutic or nutrient composition. A plunger 40 of cup-shape is provided within body 32 and, under the action of coil spring 41, it urges tablets 38 against disc 36 for access through opening 37 of the latter.

At its leading end, body 32 has opposed wings 42 pivotally connected thereto at 44; each wing 42 being of elongate strip form, and preferably rounded at its outer end. Across the leading end of body 32, there extends a curved strut 46, each end of which is pivotally connected to a respective wing 42 at 48. Strut 46 also is of elongate strip form and, as shown, has its concave surface facing toward the leading end of body 32. Preferably body 32 is formed integrally with wings 42 and strut 46, such as in the configuration shown in FIG. 4. Thereafter, strut 46 is pressed onto axial projection 50 of body 42, to secured aperture 52 of strut 46 on groove 54, behind head 56, of projection 50. With strut 46 so secured, strut 46 holds wings 42 in their operative position shown in FIG. 3 and, while the length of strut 46 enables pivoting of wings 42 to their storage position shown in FIG. 5, the compressive strength of strut 46 restrains pivoting of wings 42 from the storage position beyond the operative position.

In a variant of capsule 30, projection 50 of body 32 and aperture 52 of strut 46 are omitted. However, in such case, the locations 44 of pivotal connection of wings 42 preferably are spaced a short distance from the leading end of body 32.

The capsule 60 of FIGS. 6 to 8 has substantial overall similarity to capsule 40 of FIGS. 3 to 5. The following description therefore is with reference to the differences between capsule 40, 60.

As shown in FIGS. 6 to 8, capsule 60 has a transverse notch 62 formed across its leading end. Projecting axially from the base of notch 62, there is a pin 64 having an enlarged conical head 66. Received on pin 64, by a snap-fit over head 66, there is a hollow, rectangular abutment member 68, with a helical spring 70 on pin 64 urging member 68 away from body 72. Head 66 sets an outer limiting position for member 68, and thus acts as a stop member, while full compression of spring 70 sets an inner limiting position.

A respective wing 74, pivotally connected to body 72 at 76 extends to each side of body 72. A respective strut 78 is pivotally connected at one end to each wing 74 at 80; with each strut 78 being pivotally connected at its other end, at 82, to abutment member 68.

In urging member 68 to its outer limiting position spring 70 draws wings 74 to their operative position shown in FIG. 6. However, by movement of member 68, against the action of spring 70, wings 74 are able to move to their storage position as shown in FIG. 8. On release from their storage position wings 74 are returned to their operative position under the action of spring 70 and struts 78; although the action of head 66 in arresting movement of member 68, beyond its outer limiting position, prevents wings 74 from moving from their storage position beyond their operative position.

As shown in FIG. 7, capsule 60 preferably is formed integrally, as detailed in relation to FIG. 4 with respect of capsule 30.

In FIG. 8, there is shown a band 84 encircling body 70 and its wings with the latter in their storage position. A similar band pregerably is used with capsules 10 and 30, for storage purposes. However, secure retention of the wings in their storage position also is desirable during administering the capsule to an animal, and such band therefore preferably is retained and is of a material which is disintegrated by rumen fluids.

In each of capsules 30 and 60, wings 42, 74 have an inner portion which extends substantially at right angles to body 32, 72; although such angle may be slightly less than a right angle. At the end of those first portions, each wing 42, 74 has an outer portion which extends at a lesser angle. The arrangement is such that, with the wings in their storage position (FIGS. 5, 8), each outer wing portion is substantially parallel to the main extent of body 32, 72 and each inner portion is closely adjacent a respective axially inclined face, shown at 84 in FIGS. 6 to 8, of body 32, 72. In moving to such position, wings 42, 74 preferably simply pivot at locations 44, 76 without the need for flexing. This arrangement facilitates absorption of forces generated by rumen musculature by movement of wings 42, 74 toward their storage position, rather than away from that position beyond their operative position; the wings then being able to return to their operative position upon relaxation of those forces.

FIGS. 9 and 10 show respective variants to wings 74 for capsule 60. As shown, each wing variant 74 has an inner portion 74a to which a strut 78 is connected as in FIGS. 6 to 8, and intermediate portion 74b and an outer portion 74c. In FIG. 9, the overall wing length may be significantly greater than for the wings of capsule 60 as shwon in FIGS. 6 to 8. However, due to wing portion 74c being inclined to portion 74b, so as to extend toward the trailing end of the capsule, the overall lateral extent of the wing may be reduced. The arrangement of FIG. 10 differs from that of FIG. 9 in that portion 74b is longer, while portion 74c is shorter and extends substantially parallel to the capsule body.

In each of the variants of FIGS. 9 and 10, wing portion 74b, 74c may be pivotally interconnected such that portions 74c are pivotable from an operative position to a storage position. The operative position for portion 74c is that illustrated, while the storage position in each case is one in which portion 74c is substantially in line with its portion 74b. The memory of the material of which wings 74 are formed preferably is such that, at the junction of portion 74b, 74c, it provides a resilient bias which urges portion 74c to their operation positions. That bias is overcome by engagement of portions 74c with body 72, when the wings are in their storage position, and acts to move the wings outwardly from that position, when released, by reaction against body 72.

Either of the variants of FIGS. 9 and 10 can be used for capsule 10 of FIGS. 1 and 2 or for capsule 30 of FIGS. 3 to 5.

The capsules 30,60, apart from the means such as disc 36 for partially closing the remote end thereof, preferably are formed integrally, by injection moulding from polypropylene, polyethylene or other suitable thermoplastics material. As indicated, they are formed with wings 42,74 in an orientation such as shown in FIGS. 4, 7, although the wings as formed may extend beyond the leading end of body.

As formed, wings 42, 74 may be straight; the wings being bent to the form shown as they are moved to their storage position. Where this is the case, creep in the material of which the wings are formed will occur at the resultant bend in the wings, with the result that, on release from their storage position, the wings only partially recover. Further recovery occurs at the slightly higher temperature prevailing in the rumen, although the respective portions of each wing remain at an angle such as shown. Preferably, the angle between those portions is about 150° to 170° when recovery has occurred in the rumen. However, it is the angle those outer portions make to the longitudinal extent of the body of the capsule which is important; that angle preferably being not more than 80°, and most preferably about 70°-75°. To achieve such angle, the inner portion of each wing also may be inclined to the longitudinal extent of the body, such as up to an angle of 5° to 15°, such as about 10°.

The capsule of the invention is administered to a ruminant by injection along the oesophagus so as to lodge in the animal's rumen. The capsule is inserted axially into the oesophagus with its wings in their storage position, and with its leading end proceeding in advance of its trailing end. The wings may be held by the oesophagus in their storage position during passage of the capsule therealong. However, the wings preferably are secured in that position by a band encircling the capsule and of a material which is disintegrated by rumen fluid. When the wings are freed from the constraint of the oesophagus or of such band, they move to their operative position so as to preclude regurgitation.

Field trials with the capsule of the invention, and with known devices, have been conducted. These have established that the capsule of the invention substantially precludes regurgitation. In contrast, capsules such as disclosed in our Australian Pat. No. 520409 or of a simple T-configuration, have a retention rate with larger cattle of less than about 75% over a period of less than about 85 days.

Capsules 10, 30, 60 are suitable for use with both sheep and cattle, as well as with other ruminants. However, capsule 10 is particularly suitable for sheep, while capsule 30 or 60 is more suitable for cattle and other larger ruminants. For sheep, the capsule body preferably has a length of about 9 cm and a diameter of about 1.6 cm; while, for cattle, the corresponding dimensions preferably are about 14 cm and 2.8 cm, respectively. The overall lateral dimension for the capsule, with the wings in their operative position, is about 9 cm and 17 cm for sheep and cattle, respectively.

With the capsule of the invention retained in the rumen, fluid in the rumen is able to slowly dissolve or disintegrate the composition within the body member, by access through opening 16 (FIG. 1) or opening 37 (FIG. 3). As the composition dissolves or disintegrates, fresh composition is presented against the opening under the action of spring 41 or plunger 40. The use of a disc 36 as in FIGS. 3 to 8 is particularly advantageous, since such disc can be chosen from different ones thereof to select a disc having an opening size consistent with the required rate of dissolution or disintegration of the composition.

While a simple disc 36, located in a groove 34, has been described in relation to partial closure of the trailing end of body 32,72, other arrangements can be used. Thus, groove 34 can be omitted, with disc 36 being the bottom wall of a cup-shaped insert. In the latter case, the insert preferably is retained by its peripheral wall being force-fit within the trailing end of body 32,72.

Finally, it is to be understood that various alterations, modifications and/or additions may be introduced into the constructions and arrangements of parts previously described without departing from the spirit or ambit of the invention.

We claim:

1. A capsule for insertion into the rumen of an animal through the oesophagus and adapted to be retained therein while releasing a therapeutic or nutrient composition, said capsule comprising an elongate, tubular body member for housing a quantity of said composition, said tubular body having a leading and a trailing end; and a plurality of elongated wings, each wing being pivotally attached at one end thereof to the body member in the vicinity of the leading end of the latter; each wing being resiliently biased away from a storage position, to which it is pivotable so as to extend along the body member, toward the trailing end thereof, to a laterally extending operative position in which it is at a predetermined angle to the body member, and being constrained against pivoting beyond such angle; each of said wings
   (a) being formed integrally with the body member,
   (b) being of arcuate form transversely of its longitudinal extent to define a concave surface which, with the wing in its storage position, contacts the body member, and a convex surface remote from the concave surface; and
   (c) merging with the body member along a curved, integral hinge connection which is of a curvature corresponding substantially to the curvature of the concave and convex surfaces;
   such that it is biased to said operative position at said predetermined angle but constrained against pivoting beyond said angle.

2. A capsule according to claim 1, wherein said predetermined angle is less than 80°.

3. A capsule according to claim 1, wherein a bead is formed along each hinge connection, at the junction of the convex surface and the body member, to further constrain the wings from moving beyond their operative position.

4. A capsule according to claim 1, wherein said wings as formed are at an angle to said body member which exceeds said predetermined angle, said wings having been held in their storage position for a period such that, on release from said storage position, creep in the material of which said capsule is formed results in partial recovery of the wings to predetermined angle.

5. A capsule according to claim 1, including biasing means acting between the body member and the wings so as to normally urge the wings toward their operative position, and stop means operative to prevent movement of the wings away from their storage position, beyond the operative position.

6. A capsule according to claim 5, wherein the capsule has an abutment member located axially beyond the leading end of the body member, one of the abutment member and the body member having an axial projection slidable in an aperture of the other of those members, such that the abutment member is movable axially, toward and away from, the leading end of the body member between inner and outer limiting positions, the biasing means acting to urge the abutment member towards its outer position, and said stop means comprising an enlargement on the axial projection which limits the axial distance between those limiting positions; a respective strut member being pivotally connected at one end to each wing, with the other end of each strut member pivotally connected to the abutment member.

7. A capsule according to claim 6, wherein said projection is integral with said body member and extends from the leading end thereof, with said aperture being defined by said abutment means.

8. A capsule according to claim 7, wherein said projection is located within a transverse notch formed across said leading end.

9. A capsule according to claim 6, wherein each said wing has an inner portion by which it is pivotally connected to said body member and to which a said strut is connected, and a further portion which is inclined at a lesser angle to said body member than said inner portion.

10. A capsule for insertion into the rumen of an animal through the oesophagus and adpated to be retained therein while releasing a therapeutic or nutrient composition, said capsule comprising an elongate, tubular body member for housing a quantity of said composition and having a leading and a trailing end; and a plurality of elongate wings, each wing being pivotally attached at one end thereof to the body member in vicinity of the leading end of the latter; each wing being resiliently biased by biasing means away from a storage position, to which it is pivotable so as to extend along the body member, toward the trailing end thereof, to a laterally extending operative position in which it is at a predetermined angle to the body member, and being constrained against pivoting beyond such angle; said capsule further including strut means pivotally connected to each wing and extending across the leading end of said body member, said strut means having a length intermediate its connections to said wings sufficient to enable the wings to move from their operative position to their storage position, the compressive strength of said strut means constraining said wings from moving from said storage position beyond their operative position.

11. A capsule according to claim 20, wherein said strut means is an elongate curved strut having a concave surface facing said leading end of the body member.

12. A capsule according to claim 11, wherein said strut is connected intermediate its ends to the leading end of the body member.

13. A capsule according to claim 12, wherein said strut is so connected by means of a snap-fit engagement between a projection on one of the strut and the body member in an aperture defined by the other of said strut and the body member.

14. A capsule according to claim 10, wherein each said wing has an inner portion by which it is pivotally connected to said body member and to which said strut means is connected, and a further portion which is inclined at a lesser angle to said body member than said inner portion.

15. A capsule according to claim 14, wherein each said wing has an outermost portion which is inclined inwardly toward the trailing end of said body member.

16. A capsule according to claim 14, wherein each said wing has an outermost portion which extends substantially parallel to said body member.

17. A capsule according to claim 15, wherein said outermost portion of each wing is resiliently pivotable so as to be in line with said further portion thereof when said wings are in their storage position.

18. A capsule according to either of claims 1 or 10 formed as an integral extension.

* * * * *

UNITED STATES PATENT AND TRADEMARK OFFICE
CERTIFICATE OF CORRECTION

PATENT NO. : 4,687,480

DATED : August 18, 1987

INVENTOR(S) : Laby et al.

It is certified that error appears in the above-identified patent and that said Letters Patent is hereby corrected as shown below:

```
Col. 3, line 33, delete "oesophagus" and insert --esophagus--.
Col. 4, line 8,  delete "retions"    and insert --regions--.
Col. 5, line 26, delete "pregerably" and insert --preferably--.
Col. 7, line 31, delete "oesophagus" and insert --esophagus--.
Col. 8, line 41, delete "oespphagus" and insert --esophagus--.
```

Signed and Sealed this

Twenty-sixth Day of July, 1988

*Attest:*

DONALD J. QUIGG

*Attesting Officer*  *Commissioner of Patents and Trademarks*